US011484503B2

(12) United States Patent
Wittorff

(10) Patent No.: US 11,484,503 B2
(45) Date of Patent: *Nov. 1, 2022

(54) TABLET COMPRISING SEPARATE BINDER AND ERYTHRITOL

(71) Applicant: FERTIN PHARMA A/S, Vejle (DK)

(72) Inventor: Helle Wittorff, Vejle Øst (DK)

(73) Assignee: FERTIN PHARMA A/S, Vejle (DK)

( * ) Notice: Subject to any disclaimer, the term of this patent is extended or adjusted under 35 U.S.C. 154(b) by 85 days.

This patent is subject to a terminal disclaimer.

(21) Appl. No.: 16/682,528

(22) Filed: Nov. 13, 2019

(65) Prior Publication Data
US 2020/0078308 A1 Mar. 12, 2020

Related U.S. Application Data

(63) Continuation of application No. 15/783,722, filed on Oct. 13, 2017, now Pat. No. 10,632,076, which is a continuation-in-part of application No. 15/356,175, filed on Nov. 18, 2016, now Pat. No. 10,543,205.

(30) Foreign Application Priority Data

Nov. 18, 2016 (WO) ................ PCT/DK2016/050377

(51) Int. Cl.
A61K 9/20 (2006.01)
A61K 9/00 (2006.01)
A61K 31/455 (2006.01)

(52) U.S. Cl.
CPC .......... *A61K 9/2018* (2013.01); *A61K 9/0053* (2013.01); *A61K 9/2054* (2013.01); *A61K 9/2086* (2013.01); *A61K 31/455* (2013.01); *A61K 9/2095* (2013.01)

(58) Field of Classification Search
None
See application file for complete search history.

(56) References Cited

U.S. PATENT DOCUMENTS

| | | | |
|---|---|---|---|
| 4,627,977 A | 12/1986 | Gaffar et al. | |
| 4,820,506 A | 4/1989 | Kleinberg et al. | |
| 5,576,014 A | 11/1996 | Mizumoto et al. | |
| 5,874,068 A | 2/1999 | Engelman et al. | |
| 6,024,981 A | 2/2000 | Khankari et al. | |
| 6,146,661 A | 11/2000 | Hoshino | |
| 7,067,149 B1 | 6/2006 | Chauveau et al. | |
| 8,435,542 B2 | 5/2013 | Manley et al. | |
| 8,658,139 B1 | 2/2014 | Cutler | |
| 2003/0022912 A1 | 1/2003 | Martino et al. | |
| 2009/0311320 A1 | 12/2009 | Oury et al. | |
| 2011/0123462 A1 | 5/2011 | Mordas et al. | |
| 2011/0250247 A1 | 10/2011 | Boghmans et al. | |
| 2013/0302387 A1 | 11/2013 | Pedersen | |
| 2014/0328973 A1* | 11/2014 | Nielsen .................... A23G 4/08 426/2 |
| 2015/0101627 A1 | 4/2015 | Marshall et al. | |
| 2016/0120793 A1 | 5/2016 | Abdalla et al. | |
| 2016/0145203 A1 | 5/2016 | Gambogi et al. | |
| 2018/0140521 A1 | 5/2018 | Geonnotti et al. | |

FOREIGN PATENT DOCUMENTS

| | | | |
|---|---|---|---|
| CN | 1709229 A | 12/2005 | |
| EP | 0413427 A2 | 2/1991 | |
| EP | 0497439 A1 | 8/1992 | |
| EP | 0913148 A1 | 6/1999 | |
| EP | 0922464 A1 * | 6/1999 | ........... A61K 9/2018 |
| EP | 0922464 A1 | 6/1999 | |
| EP | 1369109 A1 | 12/2003 | |
| GB | 1526020 | 9/1978 | |
| WO | 9932092 A1 | 7/1999 | |
| WO | 02102357 A1 | 12/2002 | |
| WO | 2006063189 A2 | 6/2006 | |
| WO | 2009007768 A1 | 1/2009 | |
| WO | 2009080023 A1 | 7/2009 | |
| WO | 2010104563 A2 | 9/2010 | |
| WO | 2013125350 A1 | 8/2013 | |
| WO | 2016061486 A1 | 4/2016 | |

(Continued)

OTHER PUBLICATIONS

Signet Chemical Corp., Products, Sweetpearl, available at http://www.signetchem.com/product.aspx?prdid=1044, accessed on May 13, 2019.*
Pharmaburst® 500 ODT (available at https://www.americanpharmaceuticalreview.com/25260-Excipients/6023668-Pharmaburst-500/, accessed on May 7, 2021).*
Bolhuis GK Rexwinkel EG Zuurman K: "Polyols as filler-binders for disintegrating tablets prepared by direct compaction", Drug Development and Industrial Pharmacy, New York, NY, US, vol. 35, No. 6, Jun. 2009 (Jun. 2009), pp. 671-677, XP008162413, ISSN: 0363-9045, DOI: 10.1080/03639040802587799 the whole document.
Module. (1992) In C.G.Morris (Ed.), Academic Press Dictionary of Science and Technology. (4th ed.) [Online] Oxford: Elsevier Science & Technology. Available at http://search.credoreference.com/content/entry/apdst/module/0.
Patent Cooperation Treaty: International Search Report and Written Opinion of PCT/DK2019/050152; Gimenez Miralles, J.; dated Aug. 22, 2019; 11 pages.
Patent Cooperation Treaty: International Search Report and Written Opinion of PCT/DK2019/050153; Hartinger, Stefan; dated Sep. 30, 2019; 18 pages.

(Continued)

Primary Examiner — H. Sarah Park

(57) ABSTRACT

The invention relates to an oral delivery vehicle tablet, the delivery vehicle tablet being formed by compression of a plurality of particles, wherein the oral delivery vehicle tablet comprises sugar alcohol(s) in an amount of 40 to 99.9% by weight of the delivery vehicle tablet, wherein the oral delivery vehicle tablet comprises non-direct compressible (non-DC) erythritol particles in an amount of 15-50% by weight of the delivery vehicle tablet, wherein the oral delivery vehicle tablet comprises one or more binders other than binders granulated to the sugar alcohol(s) in an amount of 0.1 to 6% by weight of the tablet, wherein the delivery vehicle tablet comprises a plurality of further sugar alcohol particles in an amount of at least 10% by weight of the delivery vehicle tablet and wherein said further sugar alcohols particles have a composition which is different from said non-DC erythritol.

23 Claims, No Drawings

(56) References Cited

FOREIGN PATENT DOCUMENTS

| | | |
|---|---|---|
| WO | 2018091048 A1 | 5/2018 |
| WO | 2018091050 A1 | 5/2018 |

OTHER PUBLICATIONS

Patent Cooperation Treaty: International Search Report and Written Opinion of PCT/DK2019/050154; Gimenez Miralles, J.; dated Sep. 20, 2019; 12 pages.

Patent Cooperation Treaty: International Search Report and Written Opinion of PCT/DK2019/050155; Nyeki, Agnes; dated Sep. 11, 2019; 12 pages.

Patent Cooperation Treaty: International Search Report and Written Opinion of PCT/DK2019/050156; Hartinger, Stefan; dated Sep. 20, 2019; 17 pages.

Patent Cooperation Treaty: International Search Report and Written Opinion of PCT/DK2019/050157; Nyeki, Agnes; dated Sep. 16, 2019; 11 pages.

Patent Cooperation Treaty: International Search Report and Written Opinion of PCT/DK2019/050158; Gimenez Miralles, J.; dated Aug. 8, 2019; 11 pages.

Patent Cooperation Treaty: International Search Report and Written Opinion of PCT/DK2019/050159; Nyeki, Agnes; dated Aug. 22, 2019; 11 pages.

Patent Cooperation Treaty: International Search Report and Written Opinion of PCT/DK2019/050160; Hartinger Stefan; dated Sep. 20, 2019; 17 pages.

Patent Cooperation Treaty: PCT Application No. PCT/DK2017/050342: International Search Report; 6 pages; dated Nov. 30, 2017; Ceyte, Mathilde.

Patent Cooperation Treaty: PCT Application No. PCT/DK2017/050342: Written Opinion; 8 pages; dated Nov. 30, 2017 Ceyte, Mathilde.

Patent Cooperation Treaty: PTC Application No. PCT/DK2016/050377: International Search Report and Written Opinion; 12 pages; dated Aug. 3, 2017; Ceyte, Mathilde.

Roquette Product page of Sweet Pearl Maltitol USP/NF, EP, , 1 page.

Stefan W. Wessel et al.: "Potential benefits of chewing gum for the delivery of oral therapeutics and its possible role in oral healthcare", Expert Opinion on Drug Delivery, vol. 13, No. 10, Jun. 3, 2016 (Jun. 3, 2016), pp. 1421-1431, XP055609672, GB ISSN: 1742-5247, DOI: 10.1080/17425247.2016.1193154 p. 1422; table 1.

* cited by examiner

TABLET COMPRISING SEPARATE BINDER AND ERYTHRITOL

CROSS-REFERENCE TO RELATED APPLICATIONS

This application is a continuation of U.S. patent application Ser. No. 15/783,722, filed Oct. 13, 2017, entitled TABLET COMPRISING SEPARATE BINDER AND ERYTHRITOL. U.S. patent application Ser. No. 15/783,722 claims priority under 35 U.S.C. § 365 to PCT Application Serial No. PCT/DK2016/050377, filed on Nov. 18, 2016. U.S. patent application Ser. No. 15/783,722 is also a Continuation-in-Part of U.S. patent application Ser. No. 15/356,175, filed on Nov. 18, 2016, and entitled ORAL DELIVERY VEHICLE CONTAINING NICOTINE. The content of U.S. patent application Ser. Nos. 15/783,722 and 15/783,722, and PCT Application Serial No. PCT/DK2016/050377, are incorporated by reference herein in their entirety.

TECHNICAL FIELD

This disclosure relates to an oral delivery vehicle.

BACKGROUND

In the prior art it is well-known to provide oral delivery vehicles made by compression and where a substantial part of the delivery vehicle is comprised of a sugar alcohol. It is also well-known that such delivery vehicles may be very attractive for delivery of active ingredients orally. Such substances may include pharmaceuticals, nutrients, flavors, vitamins, smoke inhibitors, dietary supplements, etc.

A challenge related to such delivery vehicles is that the user of such vehicles, e.g. tablets, is more and more focused on convenience and attractive taste. Such requirements do very often conflict with what is technically possible. This is in particular relevant to delivery vehicles in the form of tablets of compressed particles.

It is an object of the invention to provide an oral delivery vehicle suitable for delivery of such active ingredients in oral cavity of a user, and it is an object to obtain a delivery vehicle which may deliver such active ingredients in the oral cavity of a user in such a way that the user finds the delivery process attractive.

SUMMARY

The invention relates to an oral delivery vehicle tablet, the delivery vehicle tablet being formed by compression of a plurality of particles, wherein the oral delivery vehicle tablet comprises sugar alcohol(s) in an amount of 40 to 99.9% by weight of the delivery vehicle tablet, wherein the oral delivery vehicle tablet comprises non-direct compressible (non-DC) erythritol particles in an amount of 15-50% by weight of the delivery vehicle tablet, wherein the oral delivery vehicle tablet comprises one or more binders other than binders granulated to the sugar alcohol(s) in an amount of 0.1 to 6% by weight of the tablet, wherein the oral delivery vehicle tablet comprises a plurality of further sugar alcohol particles in an amount of at least 10% by weight of the delivery vehicle tablet and wherein said further sugar alcohols particles have a composition which is different from said non-DC erythritol.

Binder is one of an important excipient to be added in tablet formulation. Binders are the substances that promotes cohesiveness.

In the present context, the non-DC erythritol particles are understood and defined with reference to their trade grade. Other more physical understandings, not conflicting with the above definition, as that non-DC erythritol particles are particles which has not been preprocessed by granulation with other sugar alcohols or binders for the purpose of obtaining so-called direct compressible particles (DC). Such particles of erythritol may typically consist of erythritol or at least comprise very high quantities of erythritol.

The present invention benefits from a synergy between the non-DC erythritol and the further sugar alcohol particles. The further sugar alcohols may be e.g. sorbitol which is direct compressible by nature or it may be other sugar alcohols which have been preprocessed, e.g. by granulation with a suitable binder. At the same time, the non-DC erythritol particles serves as a means for salivation which is both attractive to the user and also serves for the purpose of dissolving the further sugar alcohol particles when the tablet is chewed as fast as possible.

The use of high content of non-DC erythritol particles was not expected to work by the inventors of the present invention since the general expectation in the art of tablet pressing is that only DC grade erythritol would be possible to use in a tablet.

In the present context it is noted that the use of one or more binders other than binders which may be in the tablet and be granulated to the non-erythritol sugar alcohol(s) provides an attractive synergy with the non-DC erythritol with respect to sensorics while still obtaining a mechanically stable tablet.

The one or more binders other than binders which may be in the tablet and be granulated to the non-erythritol sugar alcohol(s) may be in the form of particles and they may therefore obtain the desired effect as separate added binder instead of requiring granulation.

In the present context, it is noted that the use of one or more separate added binders suitable for direct compression other than binders suitable for (pre)granulations which may be in the tablet and be (pre)granulated to non-erythritol sugar alcohols provides an attractive effect/combination with the non-DC erythritol with respect to sensorics while still obtaining a mechanically stable tablet.

A non-DC grade of erythritol is typically understood as a reference to commercial understanding and labeling of products and where non-DC grade is designating a product which is not considered suitable for compression. DC is within the art referring to a product enabling the manufacture of tablets of the specified or referred particles by direct compression. A non-DC composition of erythritol is typically understood as a composition comprising or consisting of particles of pure erythritol, i.e. particles which have not been subject to e.g. granulation with sugar alcohols for the purpose of obtaining particles which as commercially regarded suitable for direct compression.

The binder suitable for direct compression may be present in a tablet according to the invention as one single binder or a combination of binders. A typical content of erythritol in the individual particles of a commercially available erythritol is higher than 95%, such as 98-about 100% by weight of the individual particles.

In an embodiment of the invention the binder grade is suitable for direct compression.

When applying a binder according to the provisions of the invention, it is possible to obtain a very advantageous watering effect as these binders suitable for direct compression may then be added to the formulation without being pre-granulated to the non-DC erythritol but still contributing to the stability of the tablet without changing the sensoric and restricting the watering effect of the non-DC erythritol.

In an embodiment of the invention the non-DC erythritol particles comprises about 96-100% erythritol, such as 98-100% erythritol by weight, such as 99.5% erythritol by weight of the particles.

In an embodiment of the invention the non-DC erythritol particles are non-granulated.

Suitable binders include Gum Arabic, Methyl Cellulose, Liquid glucose, Tragacanth,Ethyl Cellulose, Gelatin, Hydroxy Propyl Methyl Cellulose (HPMC), Starches, Hydroxy Propyl Cellulose (HPC), Pregelatinized Starch, Sodium Carboxy Methyl Cellulose (NaCMC), Alginic Acid, Polyvinyl Pyrrolidone (PVP), Maltodextrine (MD); Cellulose, Polyethylene Glycol (PEG), Polyvinyl Alcohols, Polymethacrylates, Copovidone or Microcrystalline Cellulose (MCC), alone or in combination.

In an embodiment of the invention the one or more binders comprises one or more cellulose binders.

In an embodiment of the invention the one or more binders comprises microcrystalline cellulose (MCC), hydroxypropyl cellulose (HPC) or hydroxypropylmethyl cellulose (HPMC) or any combination thereof.

In an embodiment of the invention the oral tablet comprises hydroxypropyl cellulose (HPC) binder in the amount of 0.1 to 6% by weight of the tablet, such as 0.1 to 5%, such as 0.1 to 4%, such as 0.1 to 3%, such as 0.1 to 2% by weight of the tablet.

HPC may be applied as a particular attractive binder as the binder, when compared with erythritol exhibits an advantageous sensoric experience when compared to other well-known binders, such as maltodextrin. In particular, the user of HPC lower than 4% by weight of the tablet is advantageous, such as 0.1 to 3%, such as 0.1 to 2% by weight of the tablet.

In an embodiment of the invention the non-DC erythritol particles are particles that are not granulated and the one or more binders are present as separate components in the tablet.

In an embodiment of the invention the non-DC erythritol particles are particles consisting of erythritol and not being pregranulated together with the one or more binders that are present in the tablet as separate components.

According to the invention the non-DC erythritol particles are particles substantially consisting of erythritol. Thus, the single particles of non-DC erythritol available on the market may include about 96-100% erythritol, such as 98-100% by weight, such as 99.5% by weight.

In an embodiment of the invention the non-DC erythritol particles are non-granulated.

Suitable sugar alcohols typically constitute from about 40 to about 100% by weight of the tablet, such as about 80 to about 99% by weight of the tablet.

When including gum base in the formulation sugar alcohols typically constitute from about 5 to about 95% by weight of the tablet, more typically about 20 to about 80% by weight such as 30 to 70% or 30 to 60% by weight of the tablet.

High intensity artificial sweetening agents can also be used alone or in combination with the above sweeteners. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside (natural intensity sweetener) and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another tablet component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners may be used in the chewing gum formulation.

A tablet according to the invention may, if desired, include one or more fillers/texturisers including as examples, magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phosphates, cellulose polymers, such as wood, and combinations thereof.

In an embodiment of the invention the non-DC erythritol particles are non-DC grade particles, where non-DC stands for particles which are not marketed as directly compressible in a tableting process.

The use of non-DC erythritol when compared to conventionally applied direct compressible erythritol (DC) has shown remarkable effects to the users perception of the delivery vehicle when chewed. This may partly be due to the somewhat larger size of non-DC erythritol, when compared to DC-erythritol, but is may also be a result of a high content of erythritol in the individual particles applied for compression. DC-erythritol, which for obvious reasons are marketed and applied for compression purposes, does not result in such improved salivation effect and taste.

It should be noted that the terminology non-DC is easily understood within the field of technology. Suppliers or sugar alcohol provides clear guidance to the user as for the ability for use in relation to compression of tablets. A non-DC particle in this connection is referred to as a particle which is not expressly recommended by the supplier for compression. Example of a non-DC grade of erythritol is Zerose™ erythritol 16952F supplied by Cargill whereas an example of a direct compressible (DC) grade of erythritol include Zerose™ DC 16966 also supplied by Cargill.

In an embodiment of the invention the non-DC erythritol particles are defined as non-DC grade with reference to the Compressibility Index according to European Pharmacopeia 6.0 and where non-DC erythritol particles are having a compressibility index which is greater than 21%.

In an embodiment of the invention the non-DC erythritol particles are defined as non-DC with reference to the Compressibility Index according to European Pharmacopeia 6.0 and where non-DC erythritol particles are having a compressibility index which is greater than 21% and less than 37%.

In an embodiment of the invention the further sugar alcohol particles are directly compressible (DC).

The terminology directly compressible is well-known within the art of tableting, i.e. in technical field of compression of particles in a gathered compressed tablet. Directly compressible is routinely referred to as DC by many manufactures of such particles.

In an embodiment of the invention the further sugar alcohol particles are defined as DC with reference to the Compressibility Index according to European Pharmacopeia 6.0 and where said further sugar alcohol particles are having a compressibility index which is less than 21%, such as less than 15%, such as less than 10%.

In an embodiment of the invention the further sugar alcohol particles includes particles comprising sugar alcohols selected from the group of sorbitol, erythritol, xylitol, lactitol, maltitol, mannitol or isomalt or any combination thereof.

An example of such DC grade of sugar alcohol includes ISOMALT DC 101 provided by BENEO-Palatinit GmbH.

A further example of a DC grade sugar alcohol includes Zerose™ DC 16966 supplied by Cargill. It is here noted that the understanding of direct compressible is simply designated by DC. Unless otherwise stated, this terminology will be applied throughout the present application.

In an embodiment of the invention friability of the delivery vehicle tablet is less than 2%, such as less than 1.5%, wherein friability is measured according to European Pharmacopoeia 9.1, test method 2.9.7. by using a pharmaceutical friability-tester PTF 10E from Pharma Test.

According to an embodiment of the invention is has been showed that a desired friability may in fact be obtained even with a stable tablet and an attractive mouthfeel and taste. The desired mouthfeel is still obtained in spite of the fact that binders would be expected compromising the desired mouthfeel and taste in a compressed tablet and in spite of the fact that the use of the non-DC erythritol particles should compromise the friability when used in such a high amount.

In an embodiment of the invention friability of the delivery vehicle tablet is greater than 0.2%, wherein friability is measured according to European Pharmacopoeia 9.1, test method 2.9.7. by using a pharmaceutical friability-tester PTF 10E from Pharma Test.

In an embodiment of the invention said non-DC erythritol particles and said further sugar alcohol particles are of different composition, wherein said non-DC erythritol particles have an average particle size which is larger than the average particle size of said further sugar alcohol particles, wherein the average particle size is determined according to European Pharmacopoeia 9.1 when using test method 2.9.38 particle size distribution estimation by analytical sieving.

The composition of minimum two different types of sugar alcohol particles, the first sugar alcohol particles and the second sugar alcohol particles, may be different by having different chemical nature, different hygroscopicity, different solubility, different particle size, different flowability and/or different morphology may provide the user with a unique sensory experience.

In an embodiment of the invention the particle size of at least 80% of the non-DC erythritol particles is greater than 200 micron, such as greater than 225 micron, such as greater than 250 micron and wherein the particle size is determined according to European Pharmacopoeia 9.1 when using test method 2.9.38 particle size distribution estimation by analytical sieving.

According to this embodiment, it has been realized that the size of the non-DC erythritol particles features an improved salivation and mouthfeel combined with a feasible breaking force of the tablet.

In an embodiment of the invention the particle size of less than 20% of the non-DC erythritol particles is smaller than 250 micron, such as less than 15% of the non-DC erythritol particles is smaller than 250 micron, such as less than 10% of the non-DC erythritol particles is smaller than 250 micron and wherein the particle size is determined according to European Pharmacopoeia 9.1 when using test method 2.9.38 particle size distribution estimation by analytical sieving.

In an embodiment of the invention the tablet comprises more than 20% by weight of compressed non-DC erythritol particles wherein the resistance to crunching of the tablet is greater than 60N, such as greater than 70N, such as greater than 80N, such as greater than 90N, such as greater than 100 N, such as greater than 110N, such as greater than 130N such as greater than 150N, wherein the resistance to crunching of the tablet is less than 300N, such as less than 250N, such as less than 200N, wherein the resistance to crunching is determined according to European Pharmacopoeia 9.1, test method 2.9.8. by using a pharmaceutical resistance to crunching tester model Pharma Test type PTB 311.

In an embodiment of the invention the delivery vehicle tablet comprises at least one module. A module in the context of the invention is referring to a group of particles which has been compressed into a volume which is comparable to the size of the tablet. In the case of a tablet which is compressed as one module, the complete tablet is regarded as a module. A tablet comprising two or more module will thus have module sizes which each are comparable to the volume of the complete tablet. Comparable in the present context means that the modules are not understood as small particles and a module should at least be greater than 1/20 of the complete tablet volume, preferably greater than 1/10 of the complete tablet volume.

In an embodiment of the invention the delivery vehicle tablet comprises at least one module, wherein the module comprises more than 20% by weight of compressed non-DC erythritol particles, wherein the resistance to crunching of the module is greater than 60N, such as greater than 70N, such as greater than 80N, such as greater than 90N such as greater than 100 N, wherein the resistance to crunching is determined according to European Pharmacopoeia 9.1, test method 2.9.8. by using a pharmaceutical resistance to crunching tester model Pharma Test type PTB 311.

The module may typically be gathered from a plurality of compressed particles and have a weight which is greater than 0.2 gram and less than 10.

In an embodiment of the invention a module is defined as a plurality of particles being compressed together to form a gathered module of particles.

A one-module tablet, i.e. a tablet where the complete tablet is understood as a one single module, may be advantageous as the tablet from a manufacturing perspective may be easier to manufacture as the manufacturing process would not need to take into consideration the that module should be cohered with other modules.

In an embodiment of the invention the delivery vehicle tablet comprises a plurality of delivery vehicle tablet modules.

In an embodiment of the invention the plurality of modules are slice-like layers.

In an embodiment of the invention the delivery vehicle tablet comprises at least two modules, wherein the delivery vehicle tablet comprises more than 10% by weight of compressed non-DC erythritol particles, wherein the resistance to crunching of a first module comprising of compressed non-DC erythritol particles is less than 150N, wherein the resistance to crunching of a second module is more than 100N and more than the resistance to crunching of the first module, wherein the second module comprises less compressed non-DC erythritol particles with respect to weight than the first module, wherein the resistance to crunching of the delivery vehicle tablet is higher than the resistance to crunching of the second module when the second module is separated from the tablet, wherein the resistance to crunching is determined according to European Pharmacopoeia 9.1, test method 2.9.8. by using a pharmaceutical resistance to crunching tester model Pharma Test type PTB 311.

According to a further embodiment of the invention, the delivery vehicle may be in the form of a multi-module delivery vehicle. This multi-module may have the benefit that the overall hardness of the compressed delivery vehicle may be improved by the application of a module which by itself has a higher hardness than the module comprising the substantial amount of non-DC erythritol. Non-DC erythritol may have the effect that the module in which large amount of the non-Dc erythritol features a relatively low hardness. This may under certain circumstances be not desirable due to the fact that such low hardness may reflect a relatively low cohesiveness of the vehicle, thereby resulting in an increased friability of the vehicle. Under some circumstances this relatively low hardness may on the other hand reflect that the non-DC is present in substantial amounts and the low hardness may also make the non-DC easily and fast available in particular for the purposes of the second action. When applying a further module having high hardness such as a module formed by substantial amounts of compressed sugar alcohols such as sorbitol, xylitol, isomalt, etc, this support module may both delivery hardness and when broken into pieces during the initial chew benefit from the salivation effect obtained through the non-DC erythritol of the supported module. The third action, i.e. dissolving of sugar alcohols in not only obtained in the non-DC erythritol module but it is also obtained in relation to the sugar alcohols of the support module featuring less salivation effect.

Preferably, the tablet should consist of less than 5 modules, such as less than 4 modules.

In an embodiment of the invention, the tablet may be formed of two modules.

In an embodiment of the invention the oral delivery vehicle tablet comprises 0-60 percent by weight of gum base, such as 10-60 percent by weight of gum base.

An advantage of the above embodiment may be that due to the relatively fast disintegration, the chewing together of the gum base by mastication in the oral cavity of obtained relatively fast.

In an embodiment of the invention the oral delivery vehicle tablet is free of gum base.

In an embodiment of the invention the oral delivery vehicle tablet comprises a pharmaceutically active ingredient.

According to an embodiment of the invention, the obtained taste and mouthfeel facilitates an attractive masking of otherwise not to well-tasting chemical substances. One such substance is nicotine, which when delivered through the mouth may cause a sensation referred to as burning. The present invention is advantageous for taste-masking purposes. The fast salivation and significant cooling may partly taste-mask even this badly-tasting substance. Such taste-masking may of course be obtained in relation to several other chemical substances.

In an embodiment of the invention the pharmaceutically active ingredient comprises nicotine.

In an embodiment of the invention the oral delivery vehicle tablet comprises an enhancer.

In an embodiment of the invention the enhancer comprises pH controlling agent, such as buffering agent.

In an embodiment of the invention the enhancer comprises a mucoadhesive agent.

According to a further embodiment of the invention binders in separate particles may be used without compromising the advantageous taste and mouthfeel according to the invention. This is highly surprising as it appears that the presence if binders or other compression aiding substances appears to counteracts the desired effect, i.e. improved taste and mouthfeel.

In an embodiment of the invention the delivery vehicle tablet comprises flavor in an amount of 1-10% by weight of the delivery vehicle, such as 1-6% by weight of the delivery vehicle, such as 2-6% by weight of the delivery vehicle.

In embodiments of the present invention, the tablet comprises one or more flavoring agents selected from the group consisting of essential oils, essences, extracts, powders, acids, coconut, coffee, chocolate, vanilla, grape fruit, orange, lime, menthol, liquorice, caramel aroma, honey aroma, peanut, walnut, cashew, hazelnut, almonds, pineapple, strawberry, raspberry, apple, pear, peach, apricot, blackberry, cherry, pineapple, plum essence, clove oil, bay oil, anise, thyme, cedar leaf oil, nutmeg, cinnamon, peppermint, wintergreen, spearmint, *eucalyptus*, mint, or any combination thereof.

In an embodiment of the invention the flavor is a powder flavor.

In an embodiment of the invention the flavor further includes a salivation agent.

The salivation agent may e.g. include Optaflow® supplied by Symrise AG. Such agent further encourages saliva production, thereby providing improved mouthfeel and supporting base and flavor performance.

In an embodiment of the invention the weight of non-DC erythritol particles contained in the oral delivery vehicle tablet is greater than 0.3 gram, such as greater than 0.4 gram, such as greater than 0.5 gram, such as greater than 0.6 gram, such as greater than 0.7 gram, such as greater than 0.8 gram, such as greater than 0.9 gram, such as greater than 1.0 gram.

According to a further embodiment of the invention, the amount of non-DC erythritol particles is relatively high. It is in particular high when considering that the erythritol in conventional sense is not regarded attractive for compression, but the mouthfeel and salivation perceived by the user is there improved significantly, when compared to low amounts or the same amounts of DC erythritol.

In an embodiment of the invention the weight of said non-DC erythritol particles contained in the oral delivery vehicle tablet is less than 3.0 gram, such as less than 2.0 gram, such as less than greater than 1.5 gram.

In an embodiment of the invention wherein the oral delivery vehicle tablet has a weight of between 0.5 and 4.0 grams.

In an embodiment of the invention wherein the weight ratio between said non-DC erythritol particles and said further sugar alcohol particles in the delivery vehicle tablet is greater than 0.3, such as greater than 0.4, such as greater than 0.5.

The weight ratio between non-DC erythritol particles and further sugar alcohol particles has proven significant according to an embodiment of the invention in the sense that a relatively high amount of non-DC erythritol particles must be present in order to obtain the mouthfeel and taste obtained through the invention. However, this taste and mouthfeel also resides in the so-called further sugar alcohol particles. An example of such sugar alcohol particle is xylitol, which, together with the non-DC erythritol particles may provide a mouthfeel which is unique and very attractive to test panels.

In an embodiment of the invention the weight ratio between said non-DC erythritol particles and said further sugar alcohol particles in the delivery vehicle tablet is greater than 0.3, such as greater than 0.4, such as greater than 0.5 and wherein said further sugar alcohol particles are DC sugar alcohol particles.

The weight ratio between non-DC erythritol particles and further sugar alcohol particles has proven significant as mentioned above in relation to the direct sensation and mouthfeel experienced by the user, but is has moreover addressed the challenge in relation to mouthfeel when DC sugar alcohol particles crumbles during the initial chew. The mechanical stability of the tablet is much desired when the tablet is in its non-chewed form, but a fast disintegration and dissolving is desirable when the tablet is chew due to the fact that user of the tablet dislike a sandy mouthfeel induced through small hard-pressed crumbles of DC sugar alcohol. The use of a very high amount of non-DC erythritol particles will facilitate a perceived fast dissolving and disintegration of the tablet after the initial chew.

In an embodiment of the invention the weight ratio between said non-DC erythritol particles and said further sugar alcohol particles in the delivery vehicle tablet is smaller than 0.7, such as smaller than 0.6, such as smaller than 0.55.

In an embodiment of the invention the weight ratio between said non-DC erythritol particles and said further sugar alcohol particles in the delivery vehicle tablet is smaller than 0.7, such as smaller than 0.6, such as smaller than 0.55 and wherein said further sugar alcohol particles are DC sugar alcohol particles.

The weight ratio between non-DC erythritol particles and further sugar alcohol particles is important for the purpose of obtaining an advantageous taste and mouthfeel. By having an upper limit of this ratio the chewer will moreover also experience a desirable crunch sensation when starting chewing the tablet, the crunch being obtained through the use of substantial amounts of DC sugar alcohol particles and the non-DC erythritol particles.

According to an advantageous embodiment of the invention, the tablet may comprise filler.

In embodiments of the present invention, the tablet comprises filler in an amount of 0.1 to 50% by weight of the tablet, wherein the filler is hydrophobic and wherein at least 90% of the filler is contained in the tablet throughout the chewing of a user during a chewing period of at least 10 minutes.

In some embodiments of the invention, a buffer is added, the buffer being selected from the group consisting of a tris buffers, amino acid buffers, carbonate, including monocarbonate, bicarbonate or sesquicarbonate, glycerinate, phosphate, glycerophosphate, acetate, glyconate or citrate of an alkali metal, such as potassium and sodium, e.g. trisodium and tripotassium citrate, or ammonium, and mixtures thereof.

When buffer is used, a preferred buffer is sodium bicarbonate and/or sodium carbonate. In some embodiments buffer is not part of the chewing gum formulation. In some other embodiments, buffer is part of the chewing gum formulation.

In some embodiments of the invention, the amount of buffer is 0.5 to 10% by weight of the tablet.

In some embodiments of the invention the buffer is selected from the group consisting of a carbonate, including monocarbonate, bicarbonate or sesquicarbonate, glycerinate, phosphate, glycerophosphate, acetate, glyconate or citrate of an alkali metal, such as potassium and sodium, e.g. trisodium and tripotassium citrate, or ammonium, tris buffer, amino acids, and mixtures thereof.

In an embodiment of the invention the oral delivery vehicle tablet comprises said non-DC erythritol particles in an amount of 30 to 60% by weight of the tablet, said further sugar alcohol particles in an amount of 55 to 20% by weight of the tablet, erein said further sugar alcohol particles comprises xylitol, isomalt or sorbitol alone or in any combination thereof, and wherein said further sugar alcohol particles are directly compressible (DC), filler in an amount of 5 to 15% by weight of the tablet, and wherein the tablet comprises powdered flavor in an amount of 2 to 6% by weight of the tablet.

In an embodiment of the invention said further sugar alcohol comprises xylitol in an amount of more than 85% by weight of the further sugar alcohols.

In an embodiment of the invention the oral delivery tablet comprises two separate modules, wherein said modules are layers, wherein a first layer comprises said non-DC erythritol particles in an amount of 30 to 60% by weight of the modules and wherein said non-DC erythritol particles has a size which is larger than 250 micron, wherein the particle size is determined according to the European Pharmacopoeia 9.1 when using test method 2.9.38 particle size distribution estimation by analytical sieving, wherein a second layer comprises DC sugar alcohol particles in an amount of 80-100%, wherein the first layer has a resistance to crunching which is less than the resistance to crunching of the second layer and wherein the resistance to crunching is determined according to European Pharmacopoeia 9.1, test method 2.9.8. by using a pharmaceutical resistance to crunching tester model Pharma Test type PTB 311.

Moreover, the invention relates to a method of manufacturing an oral delivery vehicle according to any of the claims.

From the above it may be understood that it is possible to obtain a delivery vehicle, which, when applied as a chewing tablet may perform a fast disintegration in three different actions. The three actions are in principle not starting at the same time, and it should be understood that overlapping may occur due to the logic interaction between these actions.

The first action in this embodiment of the invention is where the user deposits the delivery vehicle in the mouth and chews the delivery vehicle. This chewing infers a mechanical crunching of the delivery vehicle. This has the consequence that the vehicle gradually, but still very fast, disintegrates into smaller distinct pieces of particles.

The second action, which is significant for obtaining the effect of this embodiment of the invention is that the non-DC erythritol has an attractive effect in the mouth of a user. It provides a cooling effect and a very attractive mouthfeel and taste for the user. Just as important is that the applied non-DC erythritol results in a significant salivation effect in the mouth of a user. This supplements the perceived mouthfeel of the user as this salivation effect is surprisingly convenient.

The third action is obtained as a result of the overall salivation effect. The salivation effect has the further benefit that smaller pieces of compressed particles of fast dissolvable sugar alcohols are dissolved faster due to the high amount of saliva. A fast dissolving of distinct particles in the mouth of the user is highly attractive to the user. Distinct particles in the mouth of a user in relation to chewing of a delivery vehicle is not perceived well by a user. It may, if the mouth feeling lasts too long result in a sandy/grain mouth feel.

Generally according to the terminology applied in the application a delivery vehicle tablet may be understood a oral tablet.

According to an advantageous embodiment of the invention, the delivery vehicle may surprisingly be compressed as a one-module delivery vehicle, where the non-DC erythritol is mixed with other sugar alcohol(s) and optional other relevant substances such as pharmaceuticals, flavors, binders etc. It has thus been shown that a delivery vehicle featuring an acceptable hardness and at the same time the desired taste and mouthfeel when chewed may be obtained.

In an embodiment of the invention, the delivery vehicle tablet may moreover comprise flavors, tableting aids, anticaking agents, emulsifiers, antioxidants, enhancers, absorption enhancers, buffers, high intensity sweeteners, softeners, colors, or any combination thereof.

In an embodiment of the invention the binder grade is suitable for direct compression.

It is advantageous that the applied binder is a grade which is suitable for direct compression when using it with non-DC erythritol.

In an embodiment of the invention the tablet comprises one or more binders in the amount of 0.1 to 3% by weight of the tablet, such as 0.1 to 2%, such as 0.1 to 1.5%, such as 0.1 to 1%, such as 0.2 to 0.5% by weight of the tablet. Even very low amounts of these binder, which are not pre-granulated to erythritol prior to compression provides a tablet having great mechanical stability and offers advantageous exploitation of the erythritol with respect to sensorics.

DETAILED DESCRIPTION

In the following raw materials will refer to the mixed particles to be compressed into a tablet according to embodiments of the invention unless otherwise stated.

The following description outlines explanations of how the inventive oral delivery vehicle tablet may be produced and further details of what may be added to the inventive composition.

Typically, the process of manufacture of the inventive oral delivery vehicle tablet may be performed in a single tablet press, such as a rotary tablet press. But it may be a benefit under some circumstances to apply a separate tablet press.

Preferably, the upper punch is convex which gives the upper face of the pressed tablet a concave form.

It should of course be noted that the shape of the punches may vary depending of the desired tablet shape.

In some embodiments of the invention, pressing of the tablets are performed at a force of 20 to 50 kN.

Important raw materials of the inventive tablet are non-DC erythritol particles and one or more further sugar alcohol particles. The further sugar alcohols particles are preferable sugar alcohols other than the non-DC erythritol particles.

In the present context, the non-DC erythritol particles are referred to as particles which has not been preprocessed by granulation with other sugar alcohols or binders for the purpose of obtaining so-called direct compressible particles.

The further sugar alcohol particles may typically refer to sugar alcohols known within the art as being direct compressible (DC).

According to a further embodiment of the invention, the applied non-DC erythritol particles is best characterized as being not-directly compressible (non-DC). The use of non-DC erythritol when compared to conventionally applied direct compressible erythritol (DC) has shown remarkable effects to the users perception of the delivery vehicle when chewed. This may partly be due to the somewhat larger size of non-DC erythritol, when compared to DC-erythritol, but is may also be a result of a high content of erythritol in the individual particles applied for compression. DC-erythritol. which for obvious reasons are marketed and applied for compression purposes, does not result in such improved salivation effect and mouthfeel.

It should be noted that the terminology non-DC is easily understood within the field of technology. Suppliers or sugar alcohol provides clear guidance to the user as for the ability for use in relation to compression of tablets. A non-DC particle in this connection is referred to as a particle which is not expressly recommended by the supplier for compression. Example of a non-DC grade of erythritol is Zerose™ erythritol 16952F supplied by Cargill whereas an example of a direct compressible (DC) grade of erythritol include Zerose™ DC 16966 also supplied by Cargill.

Direct compressible sugar alcohols may include sorbitol which is DC by nature, DC grades of Xylitol, DC grades of Erythritol, DC grades of Mannitol, DC grades of maltitol, DC grades of Lactitol, Isomalt or other suitable DC grades of sugar alcohols.

The present invention benefits from a synergy between the non-DC erythritol particles and the further sugar alcohol particles. The further sugar alcohols may be e.g. sorbitol which is direct compressible by nature or it may be other sugar alcohols which has been preprocessed, e.g. by granulation with a suitable binder, to obtain particles which when compressed may encapsulate the non-DC erythritol particles into a mechanically stable tablet. At the same time the DC erythritol particles serves as a means for salivation which is both attractive to the user and also serves for the purpose of dissolving the further sugar alcohol particles when the tablet is chewed as fast as possible.

According to embodiments of the invention, encapsulated flavors or active ingredients may be added to the final blend of raw materials prior to compression.

Different methods of encapsulating flavors or active ingredients, which may both refer to flavors or active ingredients mixed into the raw materials to be compressed into the chewing gum may e.g. include spray drying, spray cooling, film coating, coascervation, Double emulsion method (Extrusion technology) or prilling.

Materials to be used for the above-mentioned encapsulation methods may e.g. include Gelatine, Wheat protein, Soya protein, Sodium caseinate, Caseine, Gum arabic, Mod. starch, Hydrolyzed starches (maltodextrines), Alginates, Pectin, Carregeenan, Xanthan gum, Locus bean gum, Chitosan, Bees wax, Candelilla wax, Carnauba wax, Hydrogenated vegetable oils, Zein and/or Sucrose.

Preferably, these ingredients should be added subsequent to any significant heating or mixing. In other words, the active ingredients should preferably be added immediately prior to the compression of the final tablet.

If applying the present invention in relation to chewing gum, the adding of active ingredients may be cautiously blended with pre-mixed gum base granulates and further ingredients such as the ingredients stipulated by the present claims, immediately prior to the final compression of the tablet.

In one embodiment the tablet according to the invention comprises a pharmaceutically, cosmetically or biologically active substance. Examples of such active substances, a comprehensive list of which is found e.g. in WO 00/25598, which is incorporated herein by reference, include drugs, dietary supplements, antiseptic agents, pH adjusting agents, anti-smoking agents and substances for the care or treatment of the oral cavity and the teeth such as hydrogen peroxide and compounds capable of releasing urea during chewing. Examples of useful active substances in the form of antiseptics include salts and derivatives of guanidine and biguanidine (for instance chlorhexidine diacetate) and the following types of substances with limited water-solubility: quaternary ammonium compounds (e.g. ceramine, chloroxylenol, crystal violet, chloramine), aldehydes (e.g. paraformaldehyde), derivatives of dequaline, polynoxyline, phenols (e.g. thymol, p-chlorophenol, cresol), hexachlorophene, salicylic anilide compounds, triclosan, halogenes (iodine, iodophores, chloroamine, dichlorocyanuric acid salts), alcohols (3,4 dichlorobenzyl alcohol, benzyl alcohol, phenoxyethanol, phenylethanol), cf. also Martindale, The Extra Pharmacopoeia, 28th edition, pages 547-578; metal salts, complexes and compounds with limited water-solubility, such as aluminum salts, (for instance aluminum potassium sulphate AlK(SO4)2, 12H2O) and salts, complexes and compounds of boron, barium, strontium, iron, calcium, zinc, (zinc acetate, zinc chloride, zinc gluconate), copper (copper chloride, copper sulphate), lead, silver, magnesium, sodium, potassium, lithium, molybdenum, vanadium should be included; other compositions for the care of mouth and teeth: for instance; salts, complexes and compounds containing fluorine (such as sodium fluoride, sodium monofluorophosphate, aminofluorides, stannous fluoride), phosphates, carbonates and selenium. Further active substances can be found in J. Dent. Res. Vol. 28 No. 2, pages 160-171, 1949.

Examples of active substances in the form of agents adjusting the pH in the oral cavity include: acids, such as adipic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulphates or oxides of sodium, potassium, ammonium, magnesium or calcium, especially magnesium and calcium.

Active ingredients may comprise the below mentioned compounds or derivates thereof but are not limited thereto: Acetaminophen, Acetylsalicylic acid, Buprenorphine, Bromhexin, Celcoxib, Codeine, Diphenhydramin, Diclofenac, Etoricoxib, Ibuprofen, Indometacin, Ketoprofen, Lumiracoxib, Morphine, Naproxen, Oxycodon, Parecoxib, Piroxicam, Pseudoefedrin, Rofecoxib, Tenoxicam, Tramadol, Valdecoxib, Calciumcarbonat, Magaldrate, Disulfiram, Bupropion, Nicotine, Azithromycin, Clarithromycin, Clotrimazole, Erythromycin, Tetracycline, Granisetron, Ondansetron, Prometazin, Tropisetron, Brompheniramine, Ceterizin, leco-Ceterizin, Chlorcyclizine, Chlorpheniramin, Chlorpheniramin, Difenhydramine, Doxylamine, Fenofenadin, Guaifenesin, Loratidin, des-Loratidin, Phenyltoloxamine, Promethazin, Pyridamine, Terfenadin, Troxerutin, Methyldopa, Methylphenidate, Benzalcon. Chloride, Benzeth. Chloride, Cetylpyrid. Chloride, Chlorhexidine, Ecabet-sodium, Haloperidol, Allopurinol, Colchinine, Theophylline, Propanolol, Prednisolone, Prednisone, Fluoride, Urea, Actot, Glibenclamide, Glipizide, Metformin, Miglitol, Repaglinide, Rosiglitazone, Apomorfin, Cialis, Sildenafil, Vardenafil, Diphenoxylate, Simethicone, Cimetidine, Famotidine, Ranitidine, Ratinidine, cetrizin, Loratadine, Aspirin, Benzocaine, Dextrometorphan, Phenylpropanolamine, Pseudoephedrine, Cisapride, Domperidone, Metoclopramide, Acyclovir, Dioctylsulfosucc., Phenolphtalein, Almotriptan, Eletriptan, Ergotamine, Migea, Naratriptan, Rizatriptan, Sumatriptan, Zolmitriptan, Aluminum salts, Calcium salts, Ferro salts, Ag-salts, Zinc-salts, Amphotericin B, Chlorhexidine, Miconazole, Triamcinolonacetonid, Melatonine, Phenobarbitol, Caffeine, Benzodiazepiner, Hydroxyzine, Meprobamate, Phenothiazine, Buclizine, Brometazine, Cinnarizine, Cyclizine, Difenhydramine, Dimenhydrinate, Buflomedil, Amphetamine, Caffeine, Ephedrine, Orlistat, Phenylephedrine, Phenylpropanolamin, Pseudoephedrine, Sibutramin, Ketoconazole, Nitroglycerin, Nystatin, Progesterone, Testosterone, Vitamin B12, Vitamin C, Vitamin A, Vitamin D, Vitamin E, Pilocarpin, Aluminumaminoacetat, Cimetidine, Esomeprazole, Famotidine, Lansoprazole, Magnesiumoxide, Nizatide and or Ratinidine.

The invention is suitable for increased or accelerated release of active agents selected among the group of dietary supplements, oral and dental compositions, antiseptic agents, pH adjusting agents, anti-smoking agents, sweeteners, flavorings, aroma agents or drugs. Some of those will be described below.

The active agents to be used in connection with the present invention may be any substance desired to be released from the tablet. The active agents, for which a controlled and/or accelerated rate of release is desired, are primarily substances with a limited water-solubility, typically below 10 g/100 ml inclusive of substances which are totally water-insoluble. Examples are medicines, dietary supplements, oral compositions, anti-smoking agents, highly potent sweeteners, pH adjusting agents, flavorings etc.

Other active ingredients are, for instance, paracetamol, benzocaine, cinnarizine, menthol, carvone, caffeine, chlorhexidine-di-acetate, cyclizine hydrochloride, 1,8-cineol, nandrolone, miconazole, mystatine, sodium fluoride, nicotine, cetylpyridinium chloride, other quaternary ammonium compounds, vitamin E, vitamin A, vitamin D, glibenclamide or derivatives thereof, progesterone, acetylsalicylic acid, dimenhydrinate, cyclizine, metronidazole, sodium hydrogen carbonate, the active components from ginkgo, the active components from propolis, the active components from ginseng, methadone, oil of peppermint, salicylamide, hydrocortisone or astemizole.

Examples of active agents in the form of dietary supplements are for instance salts and compounds having the nutritive effect of vitamin B2 (riboflavin), B12, folinic acid, folic acid, niacine, biotine, poorly soluble glycerophosphates, amino acids, the vitamins A, D, E and K, minerals in the form of salts, complexes and compounds containing calcium, phosphorus, magnesium, iron, zinc, copper, iodine, manganese, chromium, selenium, molybdenum, potassium, sodium or cobalt.

Furthermore, reference is made to lists of nutritionists accepted by the authorities in different countries such as for instance US code of Federal Regulations, Title 21, Section 182.5013.182 5997 and 182.8013-182.8997.

Examples of active agents in the form of compounds for the care or treatment of the oral cavity and the teeth are for instance bound hydrogen peroxide and compounds capable of releasing urea during chewing.

Examples of active agents in the form of antiseptics are for instance salts and compounds of guanidine and biguanidine (for instance chlorhexidine diacetate) and the following types of substances with limited water-solubility: quaternary ammonium compounds (for instance ceramine, chloroxylenol, crystal violet, chloramine), aldehydes (for instance paraformaldehyde), compounds of dequaline, polynoxyline, phenols (for instance thymol, para chlorophenol, cresol) hexachlorophene, salicylic anilide compounds, triclosan, halogenes (iodine, iodophores, chloroamine, dichlorocyanuric acid salts), alcohols (3,4 dichlorobenzyl alcohol, benzyl alcohol, phenoxyethanol, phenylethanol), cf. furthermore Martindale, The Extra Pharmacopoeia, 28th edition, pages 547-578; metal salts, complexes and compounds with limited water-solubility, such as aluminum salts, (for instance aluminum potassium sulphate A1K(SO4) 2,12H2O) and furthermore salts, complexes and compounds of boron, barium, strontium, iron, calcium, zinc, (zinc acetate, zinc chloride, zinc gluconate), copper (copper chloride, copper sulfate), lead, silver, magnesium, sodium, potassium, lithium, molybdenum, vanadium should be included; other compositions for the care of mouth and teeth: for instance; salts, complexes and compounds containing fluorine (such as sodium fluoride, sodiummonofluorophosphate, amino fluorides, stannous fluoride), phosphates, carbonates and selenium. Cf furthermore J. Dent. Res. Vol. 28 No. 2, pages 160-171, 1949, wherein a wide range of tested compounds is mentioned.

Examples of active agents in the form of agents adjusting the pH in the oral cavity include for instance: acceptable acids, such as adipic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulfates or oxides of sodium, potassium, ammonium, magnesium or calcium, especially magnesium and calcium.

Examples of active agents in the form of anti-smoking agents include for instance: nicotine, tobacco powder or silver salts, for instance silver acetate, silver carbonate and silver nitrate.

In a further embodiment, the sucrose fatty acid esters may also be utilized for increased release of sweeteners including for instance the so-called highly potent sweeteners, such as for instance saccharin, cyclamate, aspartame, thaumatin, dihydrocalcones, stevioside, glycyrrhizin or salts or compounds thereof. For increased released of sweetener, the sucrose fatty acids preferable have a content of palmitate of at least 40% such as at least 50%.

Further examples of active agents are medicines of any type.

Examples of active agents in the form of medicines include caffeine, salicylic acid, salicyl amide and related substances (acetylsalicylic acid, choline salicylate, magnesium salicylate, sodium salicylate), paracetamol, salts of pentazocine (pentazocine hydrochloride and pentazocinelactate), buprenorphine hydrochloride, codeine hydrochloride and codeine phosphate, morphine and morphine salts (hydrochloride, sulfate, tartrate), methadone hydrochloride, ketobemidone and salts of ketobemidone (hydrochloride), beta-blockers, (propranolol), calcium antagonists, verapamil hydrochloride, nifedinpine as well as suitable substances and salts thereof mentioned in Pharm. Int., November 85, pages 267-271, Barney H. Hunter and Robert L. Talbert, nitroglycerine, erythrityl tetranitrate, strychnine and salts thereof, lidocaine, tetracaine hydrochloride, etorphine hydrochloride, atropine, insulin, enzymes (for instance papain, trypsin, amyloglucosidase, glucoseoxidase, streptokinase, streptodornase, dextranase, alpha amylase), polypeptides (oxytocin, gonadorelin, (LH.RH), desmopressin acetate (DDAVP), isoxsuprine hydrochloride, ergotamine compounds, chloroquine (phosphate, sulfate), isosorbide, demoxytocin, heparin. Other active ingredients include betalupeol, Letigen®, Sildenafil citrate and derivatives thereof.

Dental products include Carbamide, CPP Caseine Phospho Peptide; Chlorhexidine, Chlorhexidine di acetate, Chlorhexidine Chloride, Chlorhexidine di gluconate, Hexetedine, Strontium chloride, Potassium Chloride, Sodium bicarbonate, Sodium carbonate, Fluor containing ingredients, Fluorides, Sodium fluoride, Aluminum fluoride, Ammonium fluoride, Calcium fluoride, Stannous fluoride, Other fluor containing ingredients Ammonium fluorosilicate, Potassium fluorosilicate, Sodium fluorosilicate, Ammonium monofluorphosphate, Calcium monofluorphosphate, Potassium monofluorphosphate, Sodium monofluorphosphate, Octadecentyl Ammonium fluoride, Stearyl Trihydroxyethyl Propylenediamine Dihydrofluoride. Vitamins include A, B1, B2, B6, B12, Folinic acid, Folic acid, niacin, Pantothenic acid, biotine, C, D, E, K. Minerals include Calcium, phosphor, magnesium, iron, Zinc, Cupper, Iod, Mangan, Crom, Selene, Molybden. Other active ingredients include:Q10®, enzymes. Natural drugs including Ginkgo Biloba, ginger, and fish oil.

The invention also relates to use of migraine drugs such as Serotonin antagonists: Sumatriptan, Zolmitriptan, Naratriptan, Rizatriptan, Eletriptan; nausea drugs such as Cyclizin, Cinnarizin, Dimenhydramin, Difenhydrinat; hay fever drugs such as Cetrizin, Loratidin, pain relief drugs such as Buprenorfin, Tramadol, oral disease drugs such as Miconazol, Amphotericin B, Triamcinolonaceton; and the drugs Cisaprid, Domperidon, Metoclopramid. In a preferred embodiment the invention relates to the release of Nicotine and its salts.

In an embodiment of the invention, the powdered tablet materials beside the already described sugar alcohols selected from the group consisting of bulk sweeteners, flavors, dry-binders, tabletting aids, anti-caking agents, emulsifiers, antioxidants, enhancers, absorption enhancers, buffers, high intensity sweeteners, softeners, colors, or any combination thereof.

Suitable sugar alcohols typically constitute from about 40 to about 100% by weight of the tablet, such as about 80 to about 99% by weight of the tablet.

When including gum base in the formulation sugar alcohols typically constitute from about 5 to about 95% by weight of the tablet, more typically about 20 to about 80% by weight such as 30 to 70% or 30 to 60% by weight of the tablet.

High intensity artificial sweetening agents can also be used alone or in combination with the above sweeteners. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside (natural intensity sweetener) and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another tablet component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners may be used in the oral delivery vehicle formulation.

A tablet according to the invention may, if desired, include one or more fillers/texturisers including as examples, magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phos¬phates, cellulose polymers and combinations thereof.

EXAMPLES

Examples 1-7. Preparation of Oral Delivery Vehicle Tablet

TABLE 1

Oral delivery vehicle compositions for 1.6 gram tablets.
Amounts are given in wt-% of the tablet.

| Rw material (wt %) | Ex1 | Ex2 | Ex3 | Ex4 | Ex5 | Ex6 | Ex7 |
|---|---|---|---|---|---|---|---|
| Non DC Erythritol | 27.5 | 27.5 | 27.5 | 27.5 | 27.5 | 27.5 | 27.5 |
| Erythritol DC | — | — | — | — | — | — | — |
| Xylitol DC | 39 | 39 | 39 | 39 | 39 | 39 | 39 |
| Isomalt DC | 20.14 | 17.14 | 14.14 | 15.14 | 10.14 | 10.14 | 0.14 |
| CaCO3 DC | 7 | 7 | 7 | 7 | 7 | 7 | 7 |
| Flavor | 5 | 5 | 5 | 5 | 5 | 5 | 5 |
| Acesulfame-K | 0.05 | 0.05 | 0.05 | 0.05 | 0.05 | 0.05 | 0.05 |
| Sucralose | 0.15 | 0.15 | 0.15 | 0.15 | 0.15 | 0.15 | 0.15 |
| Color | 0.16 | 0.16 | 0.16 | 0.16 | 0.16 | 0.16 | 0.16 |
| Magnesium Stearate | 1 | 1 | 1 | 1 | 1 | 1 | 1 |
| HPC | — | 3 | 6 | — | — | — | — |
| CMC | — | — | — | 5 | 10 | — | — |
| MD | — | — | — | — | — | 10 | 20 |

TABLE 2

Oral delivery vehicle compositions for 1.6 gram tablets.
Amounts are given in wt-% of the tablet.

| Rw material (wt %) | Ex8 | Ex 9 | Ex10 | Ex11 | Ex12 | Ex13 |
|---|---|---|---|---|---|---|
| Non-DC Erythritol | 27.5 | 27.5 | 27.5 | 27.5 | — | 27.5 |
| Erythritol DC | — | — | — | — | 27.5 | — |
| Xylitol DC | 39 | 39 | 39 | 39 | 39 | 39 |
| Isomalt DC | 17.14 | 15.14 | 10.14 | 0.14 | 20.14 | 20.14 |
| CaCO3 DC | 7 | 7 | 7 | 7 | 7 | 7 |
| Flavor | 5 | 5 | 5 | 5 | 5 | 5 |
| Acesulfame-K | 0.05 | 0.05 | 0.05 | 0.05 | 0.05 | 0.05 |
| Sucralose | 0.15 | 0.15 | 0.15 | 0.15 | 0.15 | 0.15 |
| Color | 0.16 | 0.16 | 0.16 | 0.16 | 0.16 | 0.16 |

TABLE 2-continued

Oral delivery vehicle compositions for 1.6 gram tablets.
Amounts are given in wt-% of the tablet.

| Rw material (wt %) | Ex8 | Ex 9 | Ex10 | Ex11 | Ex12 | Ex13 |
|---|---|---|---|---|---|---|
| Magnesium Stearate | 1 | 1 | 1 | 1 | 1 | 1 |
| HPMC | 3 | 5 | — | — | — | — |
| MCC | — | — | 10 | 20 | — | — |

TABLE 3

Oral delivery vehicle compositions for 1.6 gram tablets.
Amounts are given in wt-% of the tablet.

| Rw material (wt %) | Ex14 | Ex15 | Ex16 | Ex17 | Ex18 | Ex19 | Ex20 |
|---|---|---|---|---|---|---|---|
| Non-DC Erythritol | 27.5 | 27.5 | 27.5 | 27.5 | 27.5 | 27.5 | 27.5 |
| Xylitol DC | 39 | 39 | 39 | 39 | 39 | 39 | 39 |
| Isomalt DC | 19.64 | 19.14 | 18.14 | 17.14 | 19.14 | 17.14 | 15.14 |
| CaCO3 DC | 7 | 7 | 7 | 7 | 7 | 7 | 7 |
| Flavor | 5 | 5 | 5 | 5 | 5 | 5 | 5 |
| Acesulfame-K | 0.05 | 0.05 | 0.05 | 0.05 | 0.05 | 0.05 | 0.05 |
| Sucralose | 0.15 | 0.15 | 0.15 | 0.15 | 0.15 | 0.15 | 0.15 |
| Color | 0.16 | 0.16 | 0.16 | 0.16 | 0.16 | 0.16 | 0.16 |
| Magnesium Stearate | 1 | 1 | 1 | 1 | 1 | 1 | 1 |
| HPC | 0.5 | 1 | 2 | 3 | — | — | — |
| MCC | — | — | — | — | 1 | 3 | 5 |

The materials described above are generally well-known to the person skilled within the art. As for the various tested binders, these are listed below.

HPC: Hydroxy propyl cellulose. Klucel Nutra D from Ashland; CMC: Carboxymenthyl cellulose. Walocel CRT 30 PA from Dow; MD: Maltodextrin. C Dry MD 01904 from Cargill; HPMC: Hydroxypropylmethylcellulose. Methocel K4M from Dow; MCC: Microcrystalline cellulose. Endurance MCC VE-090e from FMC.

Process Flow

The compositions indicated in the above tables 1-3 are processed into six corresponding tablets, as examples 1-20.

For each of the examples 1-20 the raw materials are sieved with a 1600 micron sieve and then weighed into the proper amount according to the exampled compositions of table 1.

The weighed amounts are then added to a Turbula mixer in a stainless steel container and blended at 50 rpm for 4 minutes and then adding magnesium stearate and blending one additional minute.

The mixtures are then tableted by means of a Piccola RIVA DC-SC-041-2. A Fette 3090i may also applied.

The resulting tablets according to Examples 1-20 are then obtained by tableting with a suitable pressure force at about 28-30 kN as main compression force.

TABLE 4

Evaluation of Examples 1-12.

| x | Resistance to crunch | Friability (%) | Processability | Sensorics | Suitable Fast dissolving Chewable tablet | WE 1-5 1 low 5 high |
|---|---|---|---|---|---|---|
| 1 Ref | 153 | 1.55 | Good | Good | Nice crunchy fast dissolving tablet Fresh taste | 5 |

TABLE 4-continued

Evaluation of Examples 1-12.

| x | Resistance to crunch | Friability (%) | Processability | Sensorics | Suitable Fast dissolving Chewable tablet | WE 1-5 1 low 5 high |
|---|---|---|---|---|---|---|
| 2 3% HPC | 167 | 0.75 | Good | Acc | Nice crunchy chew Almost as fast dissolving as reference Slightly fatty mouth feel | 4 |
| 3 6% HPC | 170 | 0.90 | Good | Poor | Slower dissolving Big residual particles in mouth for a long time Fatty mouth feel | 3 |
| 4 5% CMC | 134 | 15.3 | Acc | Poor | Sticky unpleasant feeling | 1 |
| 5 10% CMC | 167 | 3.2 | Acc | Poor | Unacceptable sticky feeling Does not dissolve or provide watering effect | 1 |
| 6 10% MD | 150 | 4.0 | Acc | Poor | A more crumble break Off taste Eryhtritol crunchiness Leaves a fatty mouthfeel on tough and teeth | 4 |
| 7 20% MD | 130 | 13.3 | Acc | Poor | A very crumble break Off taste Less crunchy Fatty mouthfeel | 3 |
| 8 3% HPMC | 160 | 0.87 | Good | Acc | Closer to standard, but slightly more fatty mouthfeel Flavor fresh mint | 4 |
| 9 5% HPMC | 163 | 1.43 | Good | Poor | Different texture, more fatty texture feeling Flavor fresh mint | 3 |
| 10 10% MCC | 167 | 1.2 | Good | Poor | Initial chew, but does not disintegrate in the right way. More fatty mouthfeel and less taste. Sticks to teeth | 3 |
| 11 20% MCC | 184 | 1.0 | Good | Poor | Unacceptable sticky Does not dissolve quickly Fatty mouth feel No fresh taste | 2 |
| 12 ERC DC | 210 | 0.8 | Poor | Poor | Too hard for a chewable tablet, does not dissolve the right way. | 3 |

WE = Watering effect,
Sensorics = Total sensory experience - Good/Acceptable(Acc)/Poor

TABLE 5

Evaluation of Examples 13-20.

| Ex | Resistance to crunch | Friability (%) | Processability | Sensorics | Suitable Fast dissolving Chewable tablet | WE 1-5 1 low 5 high |
|---|---|---|---|---|---|---|
| Ex 13 Ref | 144 | 1.42 | Good | Good | Nice crunchy fast dissolving tablet Fresh taste | 5 |
| Ex 14 0.5% HPC | 154 | 1.12 | Good | Good | Nice crunchy fast dissolving tablet Fresh taste Similar to standard | 5 |
| Ex 15 1% HPC | 162 | 0.87 | Good | Good | Nice crunchy fast dissolving tablet Fresh taste Similar to standard | 5 |
| Ex 16 2% HPC | 143 | 0.78 | Good | Acc | A bit slower dissolved Fresh and strong mint Erythritol crunchiness Very close to standard | 5 |
| Ex 17 3% HPC | 172 | 0.72 | Good | Acc | Fresh and strong mint Erythritol crunchiness A bit slower dissolved Slightly fatty mouthfeel | 5 |
| Ex 18 1% MCC | 154 | 1.06 | Good | Acc | A bit more chruncy Fresh mint Dissolve slightly different | 5 |
| Ex 19 3% MCC | 166 | 0.93 | Good | Acc | A bit more chruncy Fresh mint Dissolve slower | 5 |
| Ex 20 5% MCC | 157 | 0.80 | Good | Poor | Harder and more flaky crunch, slower dissolved A bit sticky Fresh mint | 4 |

WE = Watering effect,
Sensorics = Total sensory experience - Good/Acceptable(Acc)/Poor The examples in the above examples 1-20 of Table 4 and 5 a number of relevant parameters: Resistance to crunch given in N, Friability were measured according to European Pharmacopoeia 9.1, test method 2.9.7. by using a pharmaceutical friability-tester PTF 10E from Pharma Test, Processability were evaluated as good, acceptable or poor with respect to suitability for a process flow during manufacture of the tablets, total sensory experience were subjectively evaluated by a test panel as Good, Acceptable (Acc) or Poor, Suitability as fast dissolving chewable tablet was evaluated with a qualitative feedback from a test panel and the Watering effect was evaluated at a scale from 1-5 by a test panel, where 1 designates the lowest watering effect and 5 designates the highest watering effect.

The evaluation of the examples shows binder added to the tablets has a variable degree of effect with respect to friability. It is in particular noted that the maltodextrin (MD) of examples 6 and 7 has a very high friability of 4 and 13, 3% respectively even when used in high amounts. It is clear that such a binder is therefore not able to contain or stabilize the non-DC erythritol in the final tablet. It is moreover noted that the binder has a negative effect of the processability and also has too much off taste. It is nevertheless noted that the desired watering effect is relatively high.

It is also noted that he HPMC of examples 8, i.e. a tablet with an amount of 3% by weight of HPMC actually provides a tablet where the friability is very low, the watering effect is high, the sensory evaluation close to standard, i.e. with no binder, and the processability is acceptable.

It is also noted that HPC is even more attractive considering both sensorics, processability and friability compared to other tested binders.

The evaluation of examples 14-20 also shows that an acceptable friability, lower as around 1.2 may be obtained with different cellulose binders at the same time as an acceptable sensory evaluation and a really attractive watering effect.

What is claimed is:

1. An oral delivery vehicle tablet, the oral delivery vehicle tablet having been formed by compression of a plurality of particles, and the oral delivery vehicle tablet comprising:
   a plurality of non-directly compressible (non-DC) erythritol particles in an amount of 15 to 50% by weight of the oral delivery vehicle tablet, said plurality of non-DC erythritol particles being particles that have not been subject to granulation steps with other sugar alcohols or binders prior to said compression;
   one or more binders that are present as separate components in the oral delivery vehicle tablet in an amount of 0.1 to 6% by weight of the oral delivery vehicle tablet; and
   a plurality of further sugar alcohol particles, said plurality of further sugar alcohol particles being different in composition from said plurality of non-DC erythritol particles,
   wherein the oral delivery vehicle tablet does not comprise nicotine, and wherein a weight ratio between said plurality of non-DC erythritol particles and said plurality of further sugar alcohol particles is between 0.3 and 0.7.

2. The oral delivery vehicle tablet of claim 1, wherein said plurality of further sugar alcohol particles are directly compressible (DC) grade particles.

3. The oral delivery vehicle tablet of claim 1, wherein said plurality of further sugar alcohol particles comprise sugar alcohols selected from the group consisting of sorbitol, erythritol, xylitol, lactitol, maltitol, mannitol or isomalt or any combination thereof.

4. The oral delivery vehicle tablet of claim 1, wherein the one or more binders comprise a cellulose binder.

5. The oral delivery vehicle tablet of claim 1, wherein the one or more binders comprise microcrystalline cellulose (MCC), hydroxypropyl cellulose (HPC) or hydroxypropyl methyl cellulose (HPMC) or any combination thereof.

6. The oral delivery vehicle tablet of claim 1, wherein the one or more binders include hydroxypropyl cellulose (HPC).

7. The oral delivery vehicle tablet of claim 1, wherein the one or more binders are in an amount of 0.1 to 3% by weight of the oral delivery vehicle tablet.

8. The oral delivery vehicle tablet of claim 1, wherein friability of the oral delivery vehicle tablet is less than 2%, and wherein friability is measured according to European Pharmacopoeia 9.1, test method 2.9.7. by using a pharmaceutical friability-tester PTF 10E from Pharma Test.

9. The oral delivery vehicle tablet of claim 1, wherein the oral delivery vehicle tablet further comprising 0-60 percent by weight of gum base.

10. The oral delivery vehicle tablet of claim 1, wherein the oral delivery vehicle tablet is a chewable tablet.

11. The oral delivery vehicle tablet of claim 1, wherein the oral delivery vehicle tablet is free of gum base.

12. The oral delivery vehicle tablet of claim 1, further comprising a pharmaceutically active ingredient.

13. The oral delivery vehicle tablet of claim 1, further comprising components for care of mouth and teeth.

14. The oral delivery vehicle tablet of claim 1, further comprising a mucoadhesive agent.

15. The oral delivery vehicle tablet of claim 1, wherein the oral delivery vehicle tablet comprises a plurality of delivery vehicle tablet modules.

16. The oral delivery vehicle tablet of claim 15, wherein the oral delivery vehicle tablet comprises at least two delivery vehicle modules, wherein a resistance to crunching of a first module comprising compressed non-DC erythritol particles is less than 200N, wherein the resistance to crunching of a second module is more than 100N and more than the resistance to crunching of the first module, wherein the second module comprises less compressed non-DC erythritol particles with respect to weight than the first module, wherein the resistance to crunching of the oral delivery vehicle tablet is higher than the resistance to crunching of the second module when the second module is separated from the oral delivery vehicle tablet, and wherein the resistance to crunching is determined according to European Pharmacopoeia 9.1, test method 2.9.8. by using a pharmaceutical resistance to crunching tester model Pharma Test type PTB 311.

17. The oral delivery vehicle tablet of claim 1,
wherein the plurality of non-DC erythritol particles comprise at least 98.0% erythritol by weight of the plurality of non-DC erythritol particles.

18. The oral delivery vehicle tablet of claim 1, wherein the plurality of non-DC erythritol particles comprise at least 99.5% erythritol by weight of the plurality of non-DC erythritol particles.

19. The oral delivery vehicle tablet of claim 1, wherein at least 80% of said plurality of non-DC erythritol particles have a particle size greater than 200 micron.

20. The oral delivery vehicle tablet of claim 1, wherein less than 20% of said plurality of non-DC erythritol particles have a particle size smaller than 250 micron.

21. The oral delivery vehicle tablet of claim 1, further comprising an active ingredient selected from the group consisting of acetaminophen, acetylsalicylic acid, diphenhydramine, ibuprofen, doxylamine, guaifenesin, loratadine, dextromethorphan, caffeine, and any combination thereof.

22. The oral delivery vehicle tablet of claim 1, further comprising an active ingredient selected from the group consisting of carbamide, casein phosphopeptide, chlorhexidine, chlorhexidine diacetate, chlorhexidine chloride, chlorhexidine digluconate, hexetidine, strontium chloride, potassium chloride, sodium bicarbonate, sodium carbonate, sodium fluoride, aluminum fluoride, ammonium fluoride, calcium fluoride, stannous fluoride, ammonium fluorosilicate, potassium fluorosilicate, sodium fluorosilicate, ammonium monofluorphosphate, calcium monofluorphosphate, potassium monofluorphosphate, sodium monofluorphosphate, octadecentyl ammonium fluoride, stearyl trihydroxyethyl propylenediamine dihydrofluoride, cetylpyridinium chloride, and any combination thereof.

23. The oral delivery vehicle tablet of claim 1, further comprising an active ingredient selected from the group consisting of vitamin A, vitamin B1, vitamin B2, vitamin B6, vitamin B12, folinic acid, folic acid, niacin, pantothenic acid, biotine C, biotine D, biotine E, biotine K, zinc acetate, zinc chloride, zinc gluconate, and any combination thereof.

* * * * *